(12) United States Patent
Kim

(10) Patent No.: US 6,403,366 B1
(45) Date of Patent: Jun. 11, 2002

(54) METHOD AND APPARATUS FOR TREATING VOLATILE ORGANIC COMPOUNDS, ODORS, AND BIOGRADABLE AEROSOL/PARTICULATES IN AIR EMISSIONS

(75) Inventor: Byung Joon Kim, Champaign, IL (US)

(73) Assignee: U.S. Army Corps of Engineers as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/881,118

(22) Filed: Jun. 15, 2001

(51) Int. Cl.[7] ................................................. A61L 9/00
(52) U.S. Cl. .................. 435/266; 435/298.1; 435/299.1
(58) Field of Search .............................. 435/262.5, 266, 435/297.1, 297.2, 297.3, 298.2, 299.1; 422/177, 180; 210/619, 150; 96/288; 55/290; 261/80

(56) References Cited

U.S. PATENT DOCUMENTS

| | | | |
|---|---|---|---|
| 2,793,096 A | | 5/1957 | Pomeroy |
| 3,540,589 A | * | 11/1970 | Boris ........................ 210/150 |
| 3,880,716 A | * | 4/1975 | Engelbart et al. ..... 423/DIG. 17 |
| 4,836,918 A | * | 6/1989 | Szikriszt ..................... 210/151 |
| 4,999,302 A | | 3/1991 | Kahler et al. |
| 5,413,936 A | | 5/1995 | Rupert |
| 5,714,379 A | | 2/1998 | Phipps, Jr. |
| 5,766,938 A | | 6/1998 | Hongo |
| 5,780,293 A | | 7/1998 | Seagle |
| 6,171,853 B1 | * | 1/2001 | Kim ........................ 435/298.1 |

FOREIGN PATENT DOCUMENTS

GB   2055397 A   *   4/1981

* cited by examiner

Primary Examiner—David A. Redding
(74) Attorney, Agent, or Firm—Earl H. Baugher Jr.; Dinesh Agarwal

(57) ABSTRACT

A biofilter reactor includes a housing, an axial pipe rotatably supported in the housing and including a plurality of perforations that open into the interior of the housing for collecting a treated fluid. The axial pipe includes an outlet in communication with the interior thereof for removing the treated fluid from the housing. A porous medium is disposed about the axial pipe and is rotatable therewith. The porous medium is made of a microbial foam.

20 Claims, 7 Drawing Sheets a) Biofilter mode a) Biofilter mode b) Bioscrubber mode

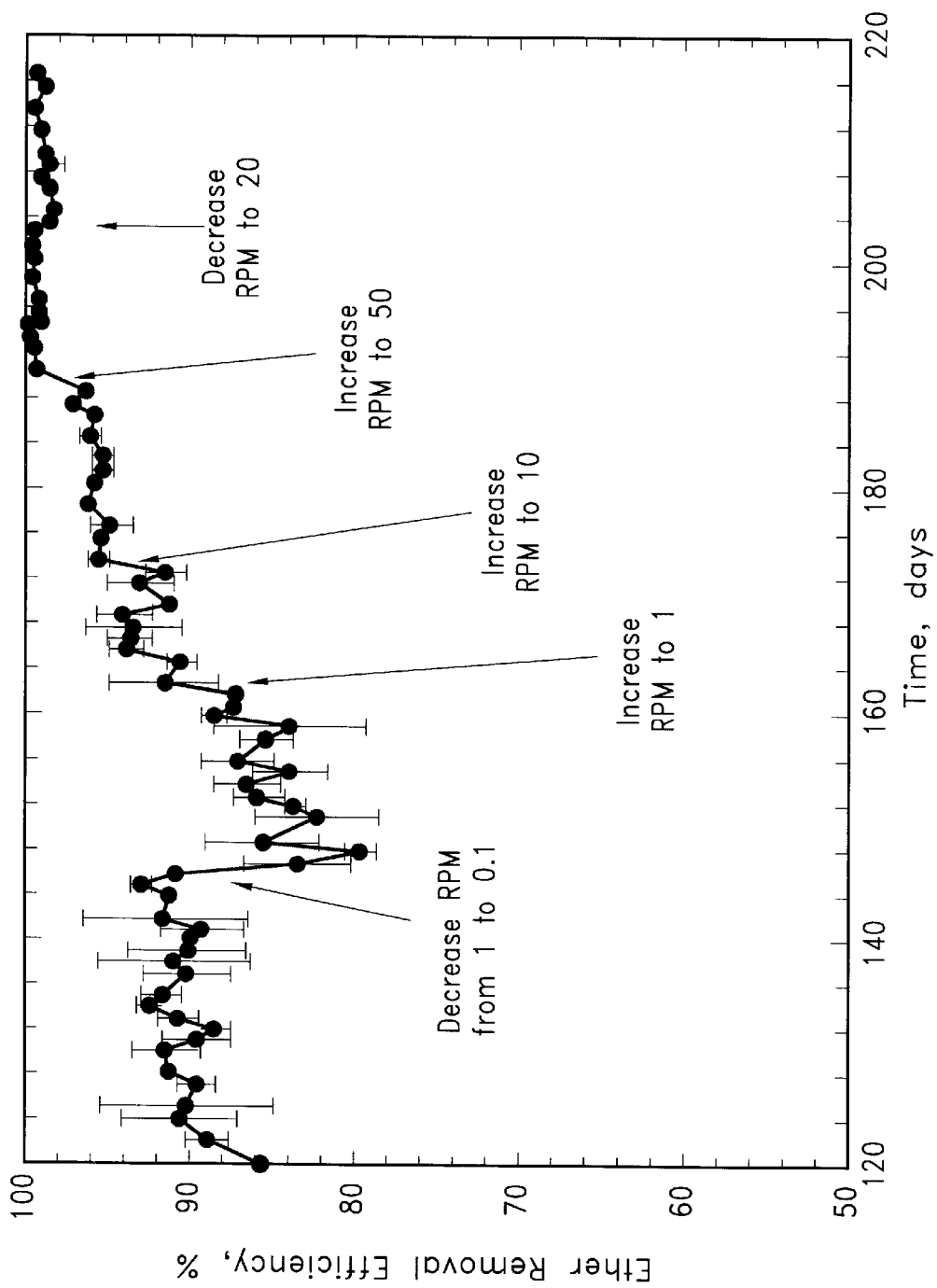
FIG. 8 LONG-TERM OPERATION WITHOUT MEDIA REPLACEMENT at EBRT of 30 sec and ether loading of 1.7 KgCOD/m³-day

METHOD AND APPARATUS FOR TREATING VOLATILE ORGANIC COMPOUNDS, ODORS, AND BIOGRADABLE AEROSOL/PARTICULATES IN AIR EMISSIONS

FIELD AND HISTORICAL BACKGROUND OF THE INVENTION

The present invention is directed to bioreactors, and more particularly to a biological method and apparatus for removing pollutants, such as volatile organic compounds, odors, and biodegradable aerosol/particulates from air emissions and convert them into carbon dioxide and water.

Existing gas-phase biological reactors use microbial metabolic reactions to treat contaminated air. Biological treatment is effective and economical for low concentrations of contaminants in large quantities of air. The contaminants are sorbed from a gas to the water/biological fixed film or suspended growth, where microbial attack occurs. Through oxidative, and occasionally reductive reactions, the contaminants are converted to carbon dioxide, water vapor, and organic biomass. Although a number of different configurations exist, the major gas-phase biological reactors are known to be biofilter, biotrickling filters, and bioscrubber (see Reference 1). In the gas-phase biological reactors, an optimized balance of contaminated air, nutrients, oxygen, waters and microbial population is a key factor for better efficiency (see References 2, 3, 4, 5, and 6).

Biofilters are not, however, filtration units, as strictly defined. Instead, they are systems that combine the basic processes of absorption, adsorption, degradation, and desorption of gas phase contaminants. A biofilter uses microorganisms fixed to media (compost, peat, etc.). As the contaminated air passes through the bed, the contaminants sorb into the biofilm and are biodegraded. Biofilters usually incorporate some form of water addition to control moisture content and add nutrients. In general, the gas stream is humidified before entering the biofilter reactor. However, if humidification proves inadequate, direct irrigation of the bed may be needed. Over time, the media tend to compact and regular replacement is needed.

A biotrickling filter uses an inorganic packing material, such as diatomaceous earth, ceramic, glass beads, etc., on which biological fixed film grows. Water is sprayed on the top of the packed bed and contaminated air is fed countercurrently or co-currently. Biotrickling filters are governed by many of the same phenomena as biofilters. However, since a biotrickling filter hosts a thriving microbiological population, excessive biomass growth and clogging are common problems.

In a bioscrubber, after initial contaminant absorption occurs, the contaminants are degraded in a separate aeration tank. Absorption of contaminants may be achieved in a packed column, spray tower, or a bubble column.

A gas-phase bioreactor is disclosed in U.S. Pat. No. 2,793,096, for using soil beds to treat odorous sewer gases. In the last ten years, more stringent environmental requirements have, however, renewed interest in gas phase biological reactors in the United States.

The following U.S. patents are directed to improving the efficiencies of existing gas-phase biological reactors.

Kahler, U.S. Pat. No. 4,999,302, rearranges a rotating biological contactor (RBC), a typical wastewater treatment unit, and feeds contaminated air into a series of chambers containing an RBC disc set. Contaminated air mainly short-circuits through the space between the RBC and the housing, and the air in the RBC disc set remains stagnant, which means that microorganisms in the unit could not be used fully.

Rupert, U.S. Pat. No. 5,413,936, provides rotation of a cylindrical vessel having a horizontal, longitudinal axis, filled with biofilter media. The purpose of rotation was to break up compacted media and to collapse any fissures. Although the rotation helps to reduce the compaction and destroy cracks, there is channeling in the media, which would be more apparent over time, and contaminated air would short-circuit.

Phipps, U.S. Pat. No. 5,714,379, generates biologically activated foam to treat contaminated air.

Hongo, U.S. Pat. No. 5,766,938, also modifies the RBC system, and uses a perforated high-density polyethylene disc with a water scooping device.

Seagle, U.S. Pat. No. 5,780,293, uses filtering media, such as activated carbon, or zeolite in a rotating drum, and passes contaminated air through a drum after it is scrubbed through a suspended growth solution. The scrubbed air escapes mainly through the space between the wall and drum and through cracks in the media.

The present invention improves the efficiency of gas-phase biological reactors by increasing the chances of meeting contaminants, oxygen, nutrients, and moisture (water) with microorganisms. Biofilters generally pass humidified, contaminated air through a thick layer of peat moss or soil. Over time, the media compacts so that contaminated air/oxygen moves through a shortcut passage or crack, and only the microorganisms present in the passage are exposed to contaminated air. This "channeling effect" means that only a limited portion of the media is actually used. Although the media material is porous, the air does not pass through the pores of the media.

Byung Kim (see Reference 7) used random shape engineered media (a flat square of polyurethane punched in the center with a circular hole and cut in half) to observe that contaminated air passed through the space between the media. Little microorganism growth occurred inside of media pores, and only the surface of the media was actively used.

The channeling effect is also a problem for the biotrickling filter. Zhu and others (see References 8, 9, 10, and 11) observed dense biomass growth in his biotrickling filter and had to backwash regularly to avoid clogging. When water is sprayed and clogging starts, water forms a channel in the biotrickling filter and contaminated air follows the channeling passages. Again, in the biotrickling filter, the microorganisms outside of the channel passage have a limited chance to contact contaminated air, oxygen, nutrients, and moisture.

Zhu and others (see References 8, 12, and 13) found nitrate was a better nitrogen source, but nitrate is a limiting factor when a highly biodegradable substance is treated. It was also found that gas-phase contaminated air can directly contact microorganisms without passing through the liquid layer. In order to overcome the nitrate-limiting condition, a gas-phase nitrogen source was suggested. In the bioscubber, the chance of water drops meeting contaminated air is also limited. In order to increase the microorganisms' chance to contact scrubbed contaminated-air, Yu and others (see References 14, 15, 16, 17) used a three-phase fluidized bed and found that suspended biomass and fixed film play different roles at different environmental conditions.

OBJECTS AND SUMMARY OF THE INVENTION

The principal object of the present invention is to provide a biofilter reactor which performs better than any other existing gas-phase biological reactor because it uses all areas of the foam media pores that are fully coated with biological fixed film. In contrast, known gas-phase biological reactors use limited surface areas of the biological fixed film due to the channeling effect.

One object of the present invention is to provide an improved biological treatment method and reactor for converting volatile organic compounds (VOCs), odors, and biodegradable aerosol/particulates in air emissions into carbon dioxide and water.

Another object of the present invention is to provide a biofilter reactor which includes all the advantages of a biofilter, a biotrickling filter, and a bioscubber. In particular, the reactor of the invention presents at least the following features:
  a. Direct contact of contaminated air with microbial film and very thin water film in air emerged cycle.
  b. Operational flexibility as a biotrickling filter. This can change nutrient content and concentrations. Water content in the media can be changed by varying rotational speed of the media.
  c. By feeding contaminated air through the inlet in the bottom housing, the reactor can be operated as a bioscrubber.

Yet another object of the present invention is to provide a biofilter reactor which has no clogging problem. A pilot system worked more than a year without clogging (see FIG. 8). Rotating the media allows excessive biomass to slough off in the submerged phase. Therefore, regular media replacement is not necessary other than from wear and tear of the media about every two years.

An additional object of the present invention is to provide a biofilter reactor which occupies a much smaller area.

Yet another object of the present invention is to provide a biofilter reactor in which media thickness (depth) is less than two inches and an air gap of less than 0.5 inches means uniform distribution of contaminated air, oxygen, water, and nutrients to the microorganisms.

Still yet another object of the present invention is to provide a biofilter reactor which is cost competitive because of its simple design.

A further object of the present invention is to provide a biofilter reactor which can operate either in a biofilter mode or a bioscrubber mode.

In summary, the main object of the present invention is to provide a biofilter reactor for removing various pollutants from a fluid. The reactor performs better than known systems and has the advantages of a biofilter, a biotrickling filter and a bioscrubber.

In accordance with the invention, a biofilter reactor includes a housing, an axial pipe rotatably supported in the housing and including a plurality of perforations that open into the interior of the housing for collecting a treated fluid. The axial pipe includes an outlet in communication with the interior thereof for removing the treated fluid from the housing. A porous medium is disposed about the axial pipe and is rotatable therewith. The porous medium is made of a microbial foam.

BRIEF DESCRIPTION OF THE DRAWINGS

The above and other objects, novel features and other advantages of the present invention will become apparent from the following detailed description of the invention, illustrated in the drawings, in which:

FIG. 8 is a graphical illustration of a test operation run with the reactor of the invention.

DETAILED DESCRIPTION OF THE INVENTION

Figure 1:
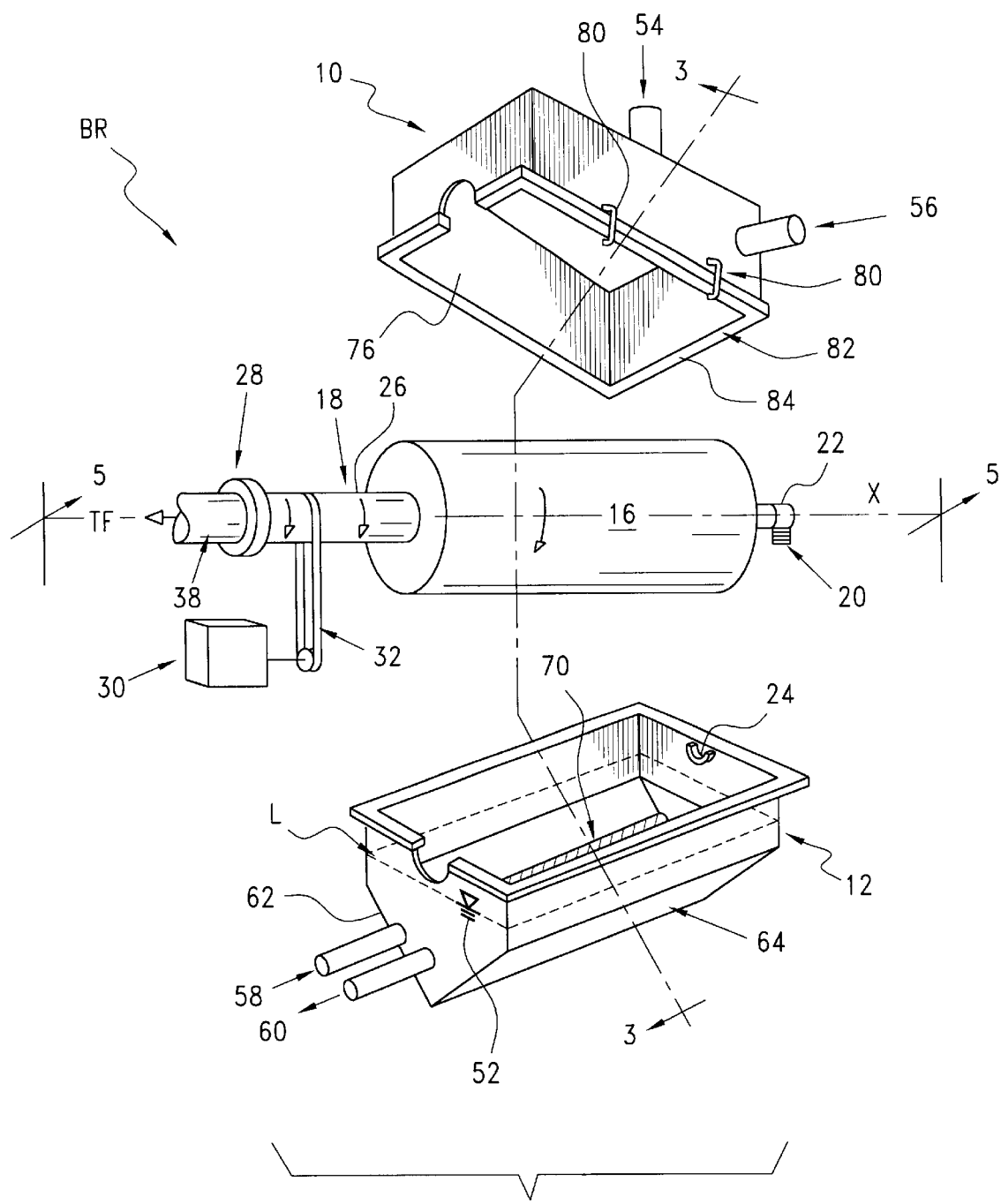
FIG. 1 is an exploded view of the reactor of the invention.
Figure 2:
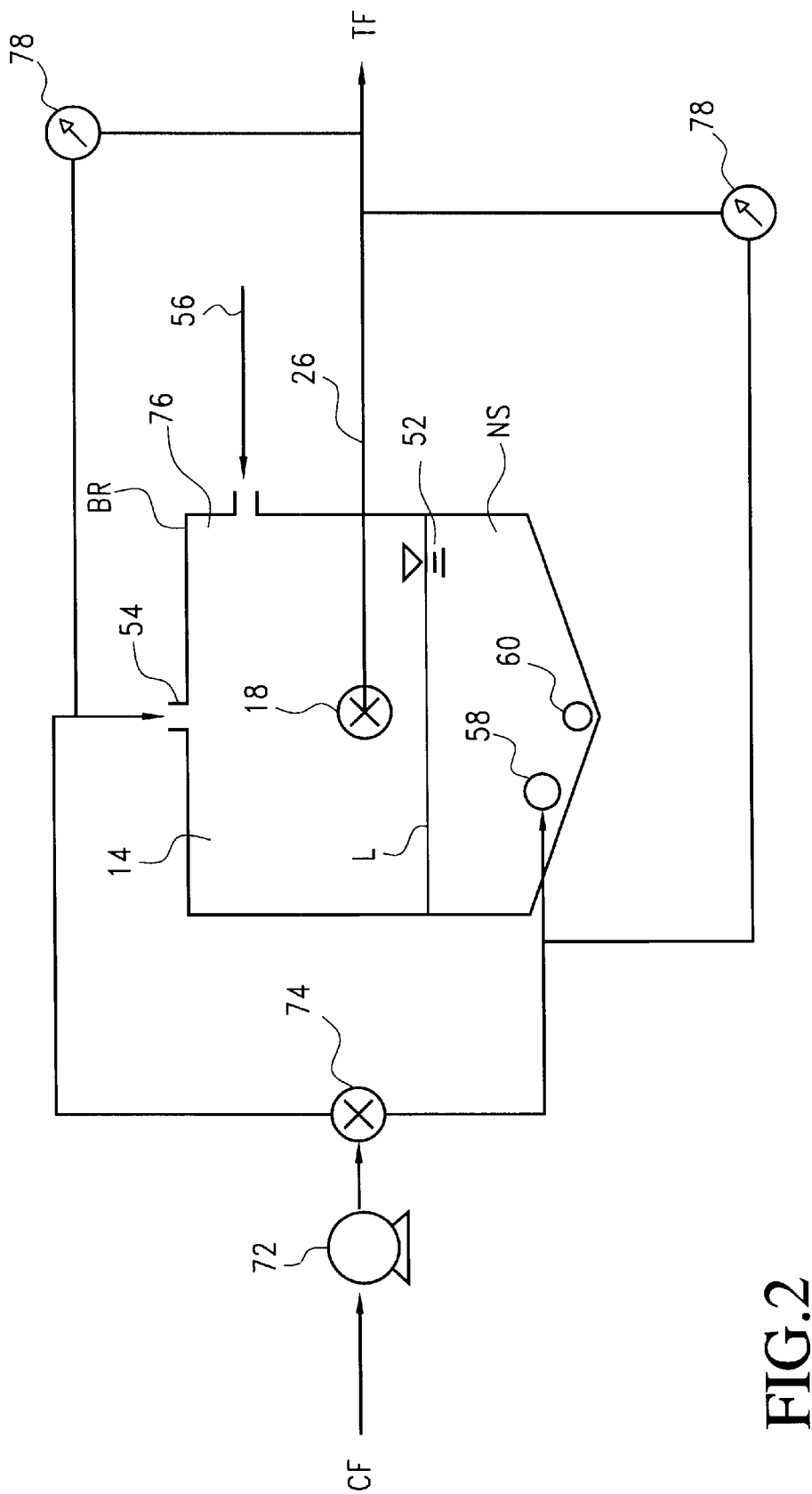
FIG. 2 is an schematic illustration showing the treatment process of the invention.

As best shown in FIG. 1, the biofilter reactor BR includes top and bottom housing sections 10 and 12, respectively, that together define an interior recess 14 (FIG. 2). A foam media unit 16 is supported on a shaft 18. The shaft 18 is rotatably mounted in the bottom housing section 12. In particular, a roller support 20, provided at an end 22 of the shaft 18, engages a bracket 24 mounted in the bottom housing section 12. The outlet end 26 of the shaft. 18 is supported exterior of the reactor BR in a conventional manner and includes a ball-bearing unit 28. A motor 30 is provided to rotate the shaft 18 by a belt 32. In this manner, when the motor 30 is actuated, the shaft 18 and the foam media unit 16, rotate about a longitudinal axis X of the shaft 18.

Figure 5:
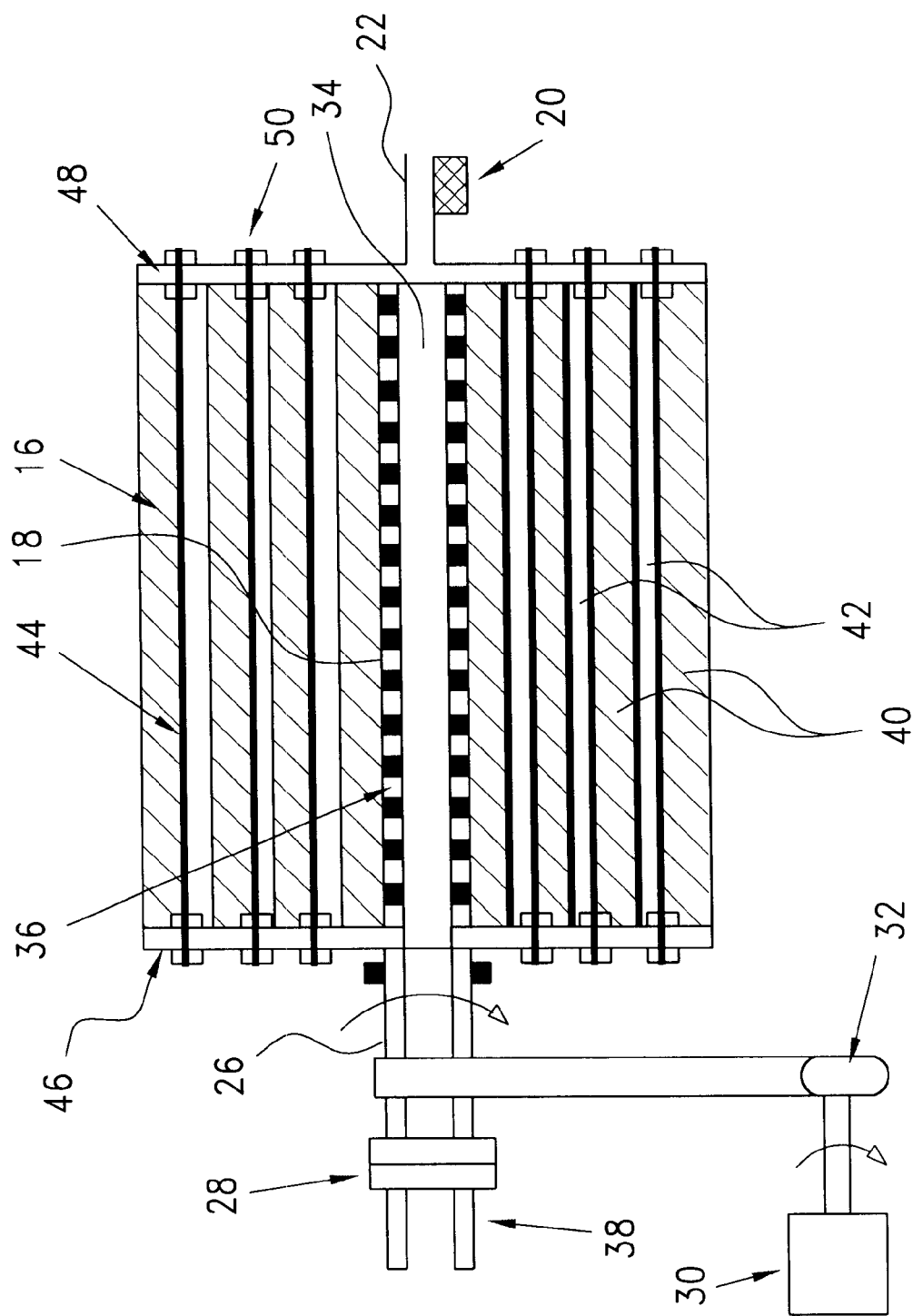
FIG. 5 is a partially enlarged cross-sectional view taken along line 5—5 of FIG. 1.

As best shown in FIG. 5, the shaft 18 is in the form of a hollow pipe with an interior recess 34, and includes perforations 36 about the periphery thereof. Therefore, the interior recess 34 of the shaft 18 is in fluid communication with the foam media unit 16 by the perforations 36. The outlet end 26 of the shaft 18 is in fluid communication with a fixed pipe 38.

Figure 3:
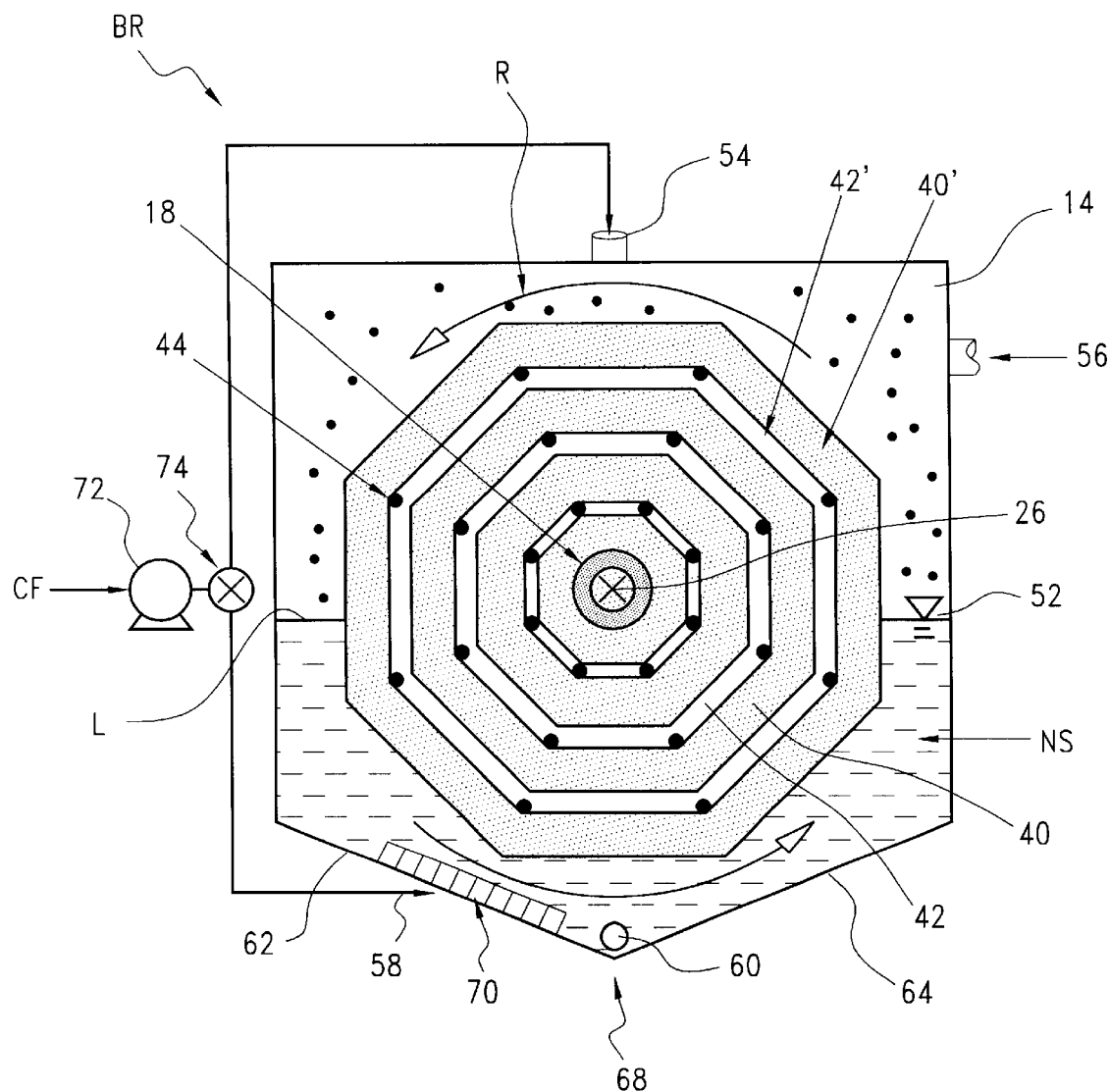
FIG. 3 is an enlarged cross-sectional view, partially schematic, taken along line 3—3 of FIG. 1.

As best shown in FIG. 3, the foam media unit 16 includes layers 40 of foam media separated by air gaps 42. The layers 40 are preferably octagonal in configuration and are supported by steel rods 44 that extend along the length of the reactor BR.

As best shown in FIG. 5, the rods 44 are mechanically fastened to left and right end plates 46 and 48 by conventional nut and bolt units 50. The end plates 46 and 48 are preferably made of stainless steel or plastic and, together with rods 44 and shaft 18, function as a frame for supporting and rotating the foam media unit 16. The end plates 46 and 48 are mechanically fastened to the shaft 18 by welding or screwing thereon, in a known manner. It is preferable that the foam media unit 16 fit tightly between the end plates 46 and 48 so that the contaminated fluid CF has to pass through the entire surface area of microbial films in the media 16.

The foam media layers 40 are preferably made of hydrophillic polyurethane with no fire-resistant chemicals or toxic substance for the microorganisms, and have 10–20 pores/inch. The media unit 16 rotates preferably in a direction R to submerge in a nutrient solution NS and, when the media 16 emerges from the solution, it carries moisture and nutrients. By changing the rotational speed, the amount of biomass attrition can be controlled and the effect of cyclic feeding can be maximized.

The foam media unit 16 has a high-concentration of microbial population in fixed film that treats the contaminated fluid CF. The importance of the rotating foam media 16 is that air contaminants, nutrients, and oxygen, are uniformly distributed to the microbial fixed film. In other words, the entire media volume is fully utilized.

As shown in FIG. 1, the top housing section includes a contaminated fluid inlet 54 and a nutrients inlet 56. Likewise, the bottom housing section 12 includes a contaminated fluid inlet 58 and a by-product or sludge/nutrient removal outlet 60.

Figure 4:
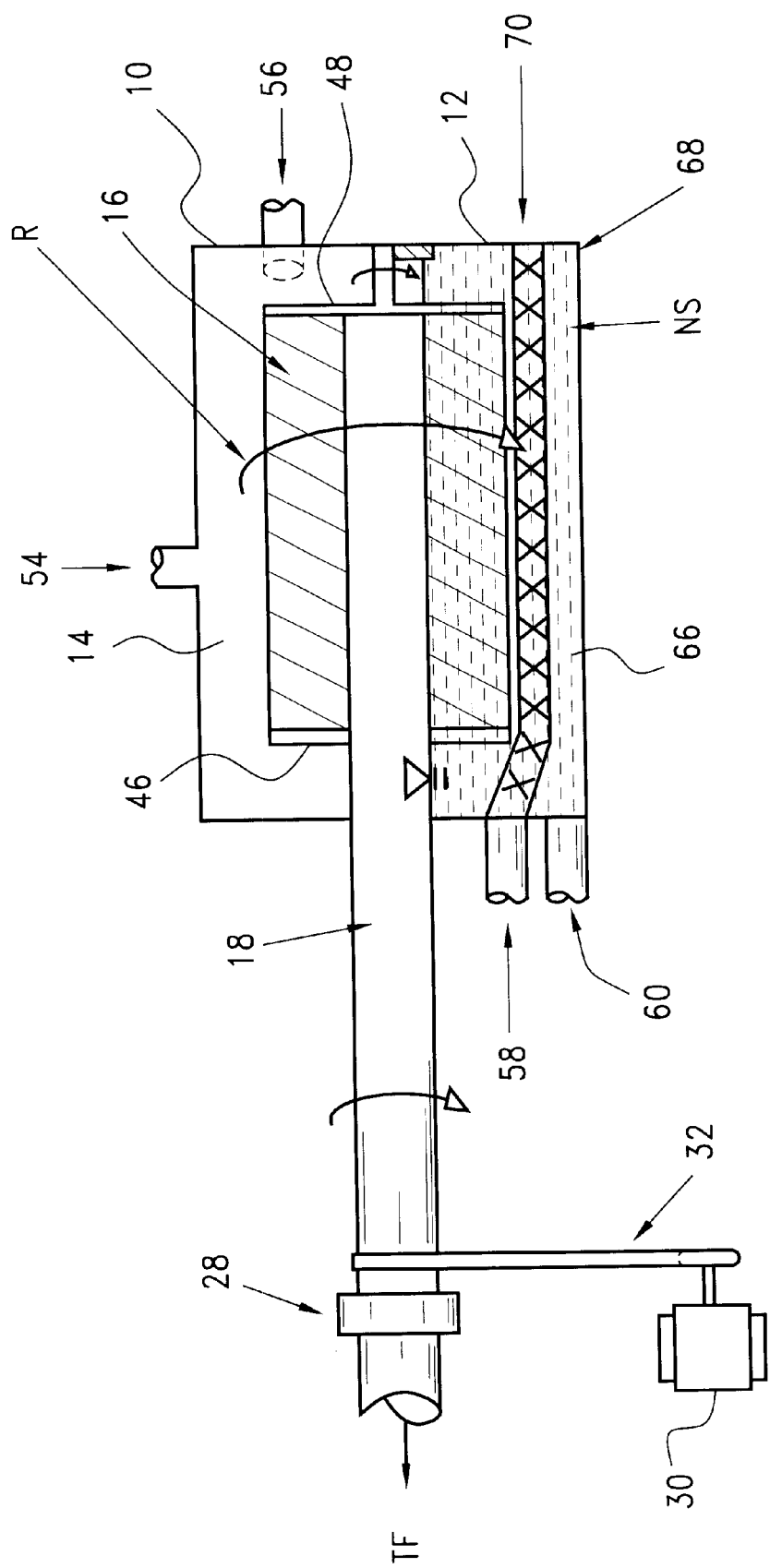
FIG. 4 is a schematic side view of FIG. 1.

As best shown in FIG. 3, the bottom housing section 12 includes downwardly sloping bottom walls 62 and 64 for easy collection of by-product or sludge generated from biological (fixed film and suspended growth) biomass. As best shown in FIG. 4, a sludge/nutrient removal pipe 66 is located at the bottommost angular portion 68 that is formed at the point where the downwardly sloping walls 62 and 64 meet (FIG. 3). The contaminated fluid inlet 58 communicates with a diffuser 70 provided on the downwardly sloping wall 62 (FIG. 3).

As best shown in FIG. 2, contaminated fluid CF is introduced into the biofilter reactor BR by a pump 72 through a valve 74. The valve 74 can be set to determine flow direction either to the headspace 76 in the top housing section 10, or into the nutrient solution NS through the inlet 58 and diffuser 70. The nutrients are introduced through the nutrient inlet 56 in the form of a liquid or gas. Treated fluid TF is collected in the shaft 18 and is discharged through the outlet 26. Pressure gauges 78 are provided to measure the pressure difference between the inlet and the outlet.

In FIG. 1, reference numeral 80 indicates clamps, and reference numeral 82 indicates a gasket provided on flange 84 of housing 10, to provide an air-tight seal, when housing sections 10 and 12 are closed together. Suitable markings 52 are provided on the lower housing section 12 to indicate solution level L.

Figure 6:
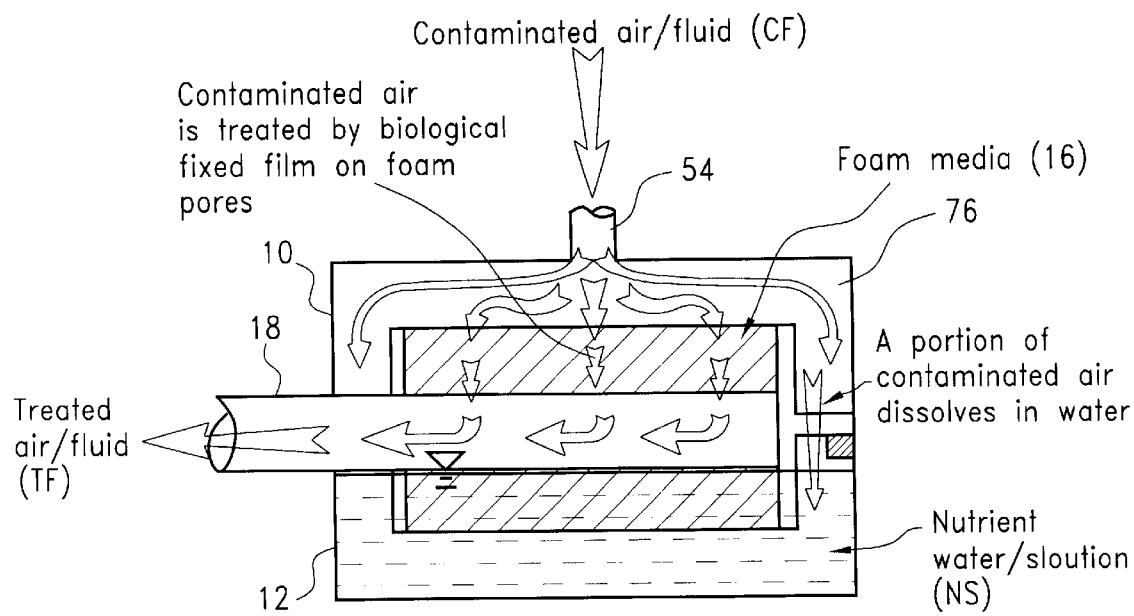
FIG. 6 is a view similar to FIG. 4, showing the reactor in a biofilter mode.
Figure 7:
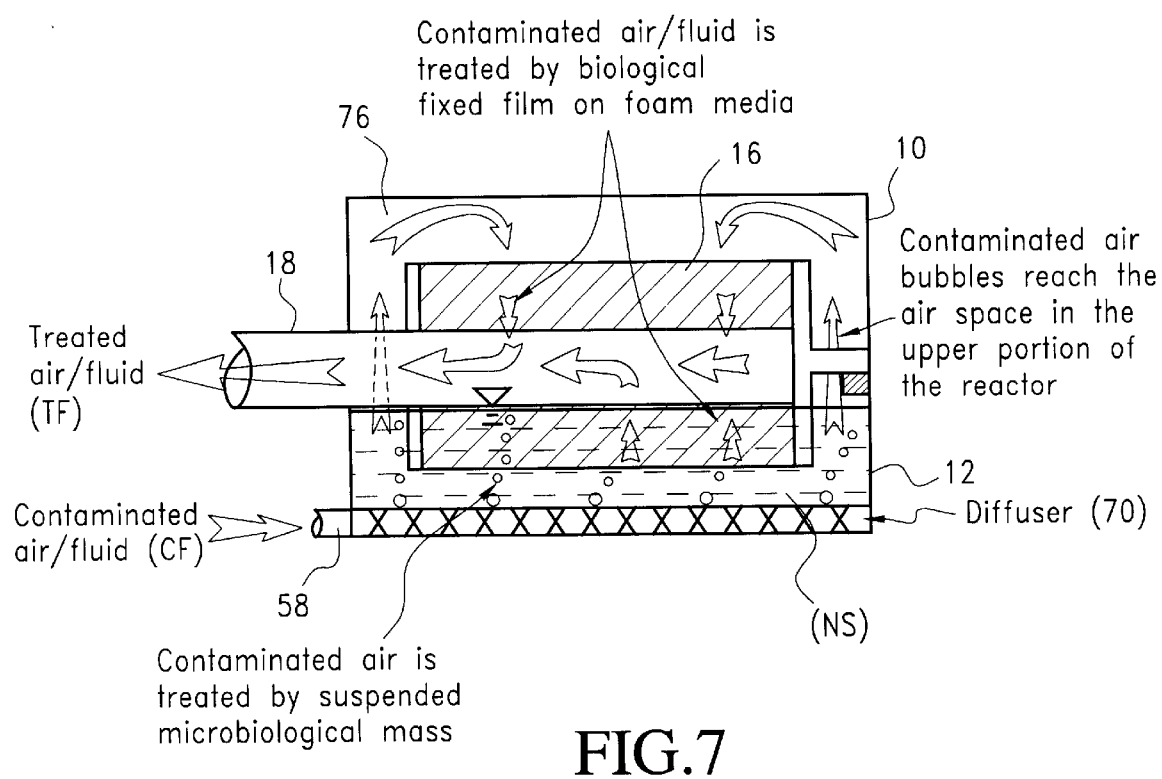
FIG. 7 is a view similar to FIG. 4, showing the reactor in a bioscrubber mode.

FIGS. 6 and 7 show two different patterns of fluid flow. In particular, FIG. 6 shows operating the biofilter reactor BR of the invention in a biofilter mode, and FIG. 7 shows the reactor BR in a bioscrubber mode.

In the biofilter mode (FIG. 6), when contaminated fluid CF is introduced into the top housing section 10 via fluid inlet 54, the fluid CF occupies the head space 76 above the nutrient solution NS. A very small portion of the contaminated fluid dissolves in the nutrient solution NS. The majority of the fluid CF passes through the microbial fixed film grown in the pores of the media 16. The contaminated fluid CF passes first through the outermost layer 40' of the media 16 with biological fixed film and is collected in the adjacent air gap 42' (FIG. 3). It then passes through the next foam layer and air gap repeatedly until the treated fluid TF is collected in the shaft 18.

In the bioscrubber mode (FIG. 7), when contaminated fluid CF is introduced through the fluid inlet 58, provided in the bottom housing section 12, and diffuser 70, into the nutrient solution NS, some of the bubbles pass through the submerged portion of the media 16 and some of the gaseous contaminants (aerosol/particulates) are scrubbed/dissolved in the nutrient solution. The remaining fluid rises up to the head space 76 in the top housing 10 and passes through the media 16, in the same fashion as in the biofilter mode (FIG. 6).

This biofilter of the invention can treat a wide array of biodegradable gaseous contaminants, aerosols, and particulates.

Examples of easily biodegradable contaminants include:
Aliphatic hydrocarbons . . . Hexane
Aromatic hydrocarbons . . . Benzene, Phenol, Toluene, Xylene, Styrene, Ethylbenzene
Chlorinated hydrocarbon . . . Dichloromethane
Nitrogen-containing carbon compounds . . . Amines, Aniline
Sulfur-containing carbon compounds . . . Carbon disulfide, Dimethylsulfide, Dimethyl disulfide
Alcohols . . . Methanol, Ethanol, Butanol, Propanol
Aldehydes . . . Formaldehyde, Acetaldehyde,
Carbonic acids . . . Butyric acid, Vinyl acetate, Ethyl acetate, Butyl acetate, Isobutyl acetate
Ethers . . . Diethyl ether, Tetrahydrofuran
Ketones . . . Acetone, Methyl ethyl ketone
Nitro ester . . . Nitroglycerin (Energetics)
Inorganic . . . Ammonia, Hydrogen sulfide
Aerosol and particulates . . . All biodegradable organic pollutants The invention offers at least the following advantages:
Operational flexibility: amount of contaminants, oxygen, nutrients, moisture can be controlled.
Polyurethane foam media (hydrophilic, with no biocide nor fire retardant) with about 10–20 pores per inch, which supports an extremely large microbial fixed film area.
High efficiency based on uniform distribution of contaminated air, nutrients, and oxygen over the biological film in the foam media.
Clog-free operation over a long time.
Tight placement of media between end plates forces contaminated air to pass through the pores of the media covered with fixed film (i.e., no shortcircuiting).
Housing has sloped bottoms to facilitate removal of sludge and nutrient solution.
Nutrient inlet, which can feed liquid nutrients as well as the gas-phase nitrogen and phosphorus. Gas nutrients may improve efficiencies during nitrogen limiting case for most easily biodegradable contaminants.
Foam media units where the shaft is used as a treated air outlet.
Rotation of media unit controls clogging by varying speed.
Capability to treat gaseous contaminants as well as aerosol and particulates.
Foam media carries water and nutrients to the fixed film. Water carrying volume can be controlled.
Short retention time (no longer than 1 minute).
Small footage requirements of equipment due to high efficiencies.
Cyclic treatment improves efficiency. Rotational speed can be varied for more effective treatment.
Sludge removal enables removal of unwanted toxic substances.
Flexibility to use biofilter and bioscrubber modes.
Feeding of contaminated air through diffusers.
Perforated tube as shaft and treated air collector.
Competitively low construction costs.

The method and reactor of the invention would have applications in all industries generating biodegradable air pollutants. Examples of such industries include: Adhesive production, ammunition manufacturing, animal husbandry, wastewater treatment plants/remediation sites, chemical and petrochemical manufacturing, food processing, and the coating, fragrance, pharmaceutical, and pulp and paper industries.

While this invention has been described as having preferred ranges, steps, materials, or designs, it is understood that it is capable of further modifications, uses and/or adaptations of the invention following in general the principle of the invention and including such departures from the present disclosure as those come within the known or customary practice in the art to which the invention pertains and as may be applied to the central features hereinbefore set forth, and fall within the scope of the invention and of the limits of the appended claims.

References:
(1) Devinny, J. S., Deshusses, M. A., Webster, T. S., Biofiltration for Air Pollution Control, Lewis Publishers, Boca Raton, N.Y. (1999)
(2) Alonso, C., Modeling of VOC Degradation in Gas Streams, Ph.D. Thesis, University of Cincinnati, (1999)
(3) Alonso, C., X. Zhu, M. T. Suidan, B. R. Kim, B. J. Kim, "Mathematical Model for the Biodegradation of VOCs in Trickle Bed Biofilters," Water Science and Technology, 39, 7 (1999): 139–146.
(4) Alonso, C., X. Zhu, M. T. Suidan, B. R. Kim, and B. J. Kim, "Mathematical Model and Parameter Estimation for Teatment of VOCs in Trickle Bed Biofilters," Proceedings of the 72nd WEF Annual Conference and Exposition, New Orleans, La. (1999).
(5) Alonso, C., M. T. Suidan, B. R. Kim, and B. J. Kim, "Dynamic Mathematical Model for the Biodegradation of VOCs in a Biofilter—Biomass Accumulation Study," Environmental Science and Technology, 32, 20 (1998): 3118–3123.
(6) Alonso, C, X. Zhu, M. T. Suidan, B. R. Kim, and B. J. Kim, "Modeling of the Biodegradation Process in a Gas Phase Bioreactor-Estimation of Intrinsic Parameters," Proceedings of the 1998 USC-TRG Conference on Biofiltration, Los Angeles, Calif. (1998).
(7) Kim, Byung J., Severin, B. F., and Neilson, L. "Biofiltration of Solvent Vapors from Munitions Manufacturing Operations", CERL Technical Report 99/57, U.S. Army Corps of Engineers, Champaign, Ill. (1999).
(8) Zhu, Xueqing, "A Fundamental Study of Biofiltration Process for VOC removal from Waste Gas Stream", Ph.D. thesis, University of Cincinnati (2000).
(9) Zhu, X, M. T. Suidan, C. Alonso, B. J. Kim, B. R. Kim, S. H. Lee, C. Yang, "The Influence of Liquid Flow Rates on VOC Removal in Trickle-Bed Biofilters," Proceedings of the AWMA Annual Meeting & Exhibition, St. Louis, Mo. (1999).
(10) Zhu, Xueqing, Suidan, M., Alonso, C., Yu, T., Kim, Byung J., and Kim Byung R. "Biofilm Structure and Mass Transfer in a Gas Phase Trickle-bed Biofilter," $1^{st}$ "World Water Congress of the International Water Association, Paris, France (to be published in Water Science and Technology) (July 2000).
(11) Zhu, X., C. A. Alonso, H. Cao, M. T. Suidan, B. J. Kim, and B. R. Kim, "The Effect of Liquid Phase on VOC Removal in Trickle-Bed Biofilters," Water Science and Technology, 38, 3 (1998): 315–322.
(12) Rihn, M. J., X. Zhu, M. T. Suidan, B. J. Kim, and B. R. Kim, "The Effect of Nitrate on VOC Removal in Trickle Bed Biofilters," Water Research, 31, 2997–3008 (1997).
(13) Zhu, X, M. J. Rihn, M. T. Suidan, B. J. Kim, and B. R. Kim, "The Effect of Nitrate on VOC Removal in Trickle Bed Biofilters," Water Science and Technology, 34, 34 (1996): 573–581.
(14) Fim, Byung J., Yu, H., and Rittman, B., "Treatment of Volatile Organic Compounds from Gas Streams Using a Three-Phase Circulating-Bed Biofilm Reactor", ERDC/CERL TR-00-9, U.S. Army Corps of Engineers, Champaign, Ill. (2000).
(15) Yu, H., Kim, B., and Rittmann, B., "Contributions of Biofilm Versus Suspended Bacteria in an Aerobic Circulating Bed Biofilm Reactor," 1st World Water Congress of the International Water Association, Paris, France (to be published in Water Science and Technology) (July 2000).
(16) Yu, H., B. J. Kim, and B. E. Rittmann, "Gas Phase Toluene Removal by Circulating Bed Biofilm Reactor," International Specially Conference on Biofilm Processes, International Association on Water Qulity, New York (November 1999).
(17) Yu, H., B. J. Kim, and B. E. Rittmann. "Effects of Substrate and Oxygen Limitation on Gas-phase Toluene Removal in a Three-phase Biofilm Reactor," Water Science and Technology, in press.

What is claimed is:

1. A biofilter reactor for removing pollutants from a fluid, comprising:
   a) a housing;
   b) an axial pipe rotatably supported in said housing and including a plurality of perforations that open into the interior of said housing for collecting a treated fluid;
   c) said axial pipe including an outlet in communication with the interior thereof for removing the treated fluid from said housing;
   d) a porous medium disposed about said axial pipe and rotatable therewith; and
   e) said porous medium comprising a microbial foam medium.

2. The biofilter of claim 1, wherein:
   a) said housing includes a sloped bottom portion for collecting by-product; and
   b) a by-product removal outlet operably connected to said sloped portion.

3. The biofilter of claim 1, wherein:
   a) said housing comprises upper and lower housing portions; and
   b) first and second contaminated fluid inlets operably connected to said housing.

4. The biofilter of claim 3, wherein:
   a) said first fluid inlet is operably connected to said upper housing portion; and
   b) said second fluid inlet is operably connected to said lower housing portion.

5. The biofilter of claim 4, further comprising:
   a) a diffuser positioned in said lower housing portion and in operable fluid communication with said second fluid inlet.

6. The biofilter of claim 1, wherein:
   a) said porous medium comprises at least two layers separated by an air gap.

7. The biofilter of claim 6, further comprising:
   a) first and second end plates mounted to said axial pipe; and
   b) wherein said porous medium is positioned between said first and second end plates.

8. The biofilter of claim 1, wherein:
   a) said foam medium comprises a hydrophilic polyurethane foam.

9. The biofilter of claim 8, wherein:
   a) said foam medium is substantially free of a toxin or fire-resistant material.

10. A biofilter reactor for removing pollutants from a fluid, comprising:
 a) a housing including upper and lower portions;
 b) an axial pipe rotatably supported in said housing and including a plurality of perforations that open into the interior of said housing for collecting a treated fluid;
 c) said axial pipe including an outlet in communication with the interior thereof for removing the treated fluid from said housing;
 d) first and second axially spaced end plates mounted to said axial pipe;
 e) a microbial foam medium positioned between said first and second end plates; and
 f) said lower housing portion including a sloped portion for collecting by-product.

11. The biofilter of claim 10, further comprising:
 a) a by-product removal outlet operably connected to said sloped portion.

12. The biofilter of claim 11, wherein:
 a) said foam medium comprises at least two layers separated by an air gap.

13. The biofilter of claim 12, wherein:
 a) said foam medium comprises a hydrophilic polyurethane foam.

14. The biofilter of claim 13, wherein:
 a) said foam medium is substantially free of a toxin or fire-resistant material.

15. The biofilter of claim 13, wherein:
 a) said foam medium comprises about 10–20 pores/inch.

16. The biofilter of claim 10, further comprising:
 a) first and second contaminated fluid inlets operably connected to said upper and lower housing portions, respectively.

17. The biofilter of claim 16, further comprising:
 a) a diffuser in operable fluid communication with said second fluid inlet.

18. A method of removing pollutants from a fluid, comprising the steps of:
 a) providing a biofilter reactor, comprising:
  i) a housing including upper and lower portions;
  ii) an axial pipe rotatably supported in said housing and including a plurality or perforations that open into the interior of said housing for collecting a treated fluid;
  iii) said axial pipe including an outlet in communication with the interior thereof for removing the treated fluid from said housing;
  iv) first and second axially spaced end plates mounted to said axial pipe and rotatable therewith;
  v) a microbial foam medium positioned between said first and second end plates and rotatable with said axial pipe;
  vi) said lower housing portion including a sloped portion for collecting by-product;
  vii) a fluid inlet operably connected to said housing; and
  viii) a by-product removal outlet operably connected to said sloped portion;
 b) introducing a contaminated fluid into the housing through the the fluid inlet;
 c) removing contaminants by passing the contaminated fluid through the foam medium and assimilating the pollutants and producing a by-product;
 d) collecting the by-product in the sloped portion of the lower housing portion and removing through the by-product removal outlet; and
 e) collecting the treated fluid in the axial pipe and removing through the outlet thereof.

19. The method of claim 18, further comprising the step of:
 f) introducing a nutrient into the housing prior to step b), through a nutrient inlet operably connected to said upper housing portion.

20. A method of removing pollutants from a fluid, comprising the steps of:
 a) providing a biofilter reactor, comprising:
  i) a housing including upper and lower portions;
  ii) an axial pipe rotatably supported in said housing and including a plurality or perforations that open into the interior of said housing for collecting a treated fluid;
  iii) said axial pipe including an outlet in communication with the interior thereof for removing the treated fluid from said housing;
  iv) first and second axially spaced end plates mounted to said axial pipe and rotatable therewith;
  v) a microbial foam medium positioned between said first and second end plates and rotatable with said axial pipe;
  vi) said lower housing portion including a sloped portion for collecting by-product;
  vii) first and second fluid inlets operably connected to said upper and lower portions of said housing, respectively; and
  viii)) a by-product removal outlet operably connected to said sloped portion;
 b) introducing a contaminated fluid into the housing through one of the first and second fluid inlets;
 c) removing contaminants by passing the contaminated fluid through the foam medium and assimilating the pollutants and producing a by-product;
 d) collecting the by-product in the sloped portion of the lower housing portion and removing through the by-product removal outlet; and
 e) collecting the treated fluid in the axial pipe and removing through the outlet thereof.

* * * * *